United States Patent [19]

Lee, Jr. et al.

[11] 4,221,698

[45] Sep. 9, 1980

[54] CARVABLE DENTAL RESTORATIVE COMPOSITIONS

[75] Inventors: Henry L. Lee, Jr., Pasadena; Jan A. Orlowski, Altadena, both of Calif.

[73] Assignee: Lee Pharmaceuticals, South El Monte, Calif.

[21] Appl. No.: 906,926

[22] Filed: May 18, 1978

Related U.S. Application Data

[63] Continuation of Ser. No. 669,174, Mar. 22, 1976, abandoned, which is a continuation of Ser. No. 504,838, Sep. 10, 1974, abandoned.

[51] Int. Cl.$^2$ .......................... C08K 3/34; C08K 3/36; C08K 3/40
[52] U.S. Cl. .............................. 260/42.52; 433/228; 260/42.43; 260/42.53; 260/998.11
[58] Field of Search ............... 260/42.15, 42.52, 42.53, 260/998.11, DIG. 36, 42.43; 32/15

[56] References Cited

U.S. PATENT DOCUMENTS

| | | | |
|---|---|---|---|
| 2,335,133 | 11/1943 | Renfrew | 260/84 |
| 2,580,901 | 1/1952 | Erickson et al. | 260/86.7 |
| 3,066,112 | 11/1962 | Bowen | 260/41 |
| 3,179,623 | 4/1965 | Bowen | 260/47 |
| 3,194,783 | 7/1965 | Bowen | 260/41 |
| 3,442,851 | 5/1969 | McManimie | 260/41 |
| 3,539,526 | 11/1970 | Bowen | 260/47 |
| 3,539,533 | 11/1970 | Lee et al. | 260/47 |
| 3,597,389 | 8/1971 | Taylor | 260/41 |
| 3,629,187 | 12/1971 | Waller | 260/41 R |
| 3,679,447 | 7/1972 | Aronoff et al. | 106/287 |
| 3,751,399 | 8/1973 | Lee | 260/47 UA |
| 3,819,568 | 6/1974 | Taylor et al. | 260/42.52 |
| 3,825,518 | 7/1974 | Foster et al. | 260/42.52 |
| 3,926,906 | 12/1975 | Lee et al. | 260/42.53 |
| 3,971,754 | 7/1976 | Jurecic | 260/42.15 |

*Primary Examiner*—Stanford M. Levin
*Attorney, Agent, or Firm*—Irons and Sears

[57] ABSTRACT

Dental restorative compositions comprise self-curing systems of monomer containing two or more polymerizable ethylenically unsaturated groups of different respective reactivities, and thus of different curing rates, and other materials such as fillers, inhibitors, curing agents, and the like. The polymerizable groups may be selected from the group consisting of two or more vinyl, allyl, acryl, methacryl, and styryl groups.

6 Claims, No Drawings

CARVABLE DENTAL RESTORATIVE COMPOSITIONS

RELATED APPLICATIONS

This application is a continuation of Ser. No. 669,174, filed Mar. 22, 1976, now abandoned, which in turn was a continuation of Ser. No. 504,838, filed Sept. 10, 1974, and now abandoned.

BACKGROUND OF THE INVENTION

1. Field of the Invention:

The present invention relates to improved compositions of matter for restoring prepared teeth, which can be easily carved into a replica of the original anatomical form. More particularly, the present invention contemplates compositions of matter comprised of a conventional filler and a polymerizable monomeric substance having two or more polymerizable groups which react at different rates. The polymerizable substance may be comprised of a monomer having within its structure the two or more polymerizable groups, or a mixture of monomers, of different reactivity. Groups are selected having a reactivity such that the compositions will polymerize to achieve a Shore D hardness of about 85 at least in two minutes, but preferably within about twelve minutes, after reaching Shore D hardness of about 45 at 37° C., thus permitting the dentist ample time to shape the restoration using conventional carving techniques.

2. Description of the Prior Art:

Dental amalgam has been used for dental restorations for over a century, and is still used in about three-fourths of all restorations. More recently developed composite restoratives comprised of a filler and a polymerizable monomer, while superior to amalgam in many respects, have replaced amalgam to only a limited extent due at least in part to the difficulty in shaping of these compositions to a replica of the original occlusal surface.

In a Class II cavity preparation, a considerable amount of the occlusal surface is involved along with at least one of the proximal surfaces. It is very important to the proper functioning of the tooth that these surfaces be restored to their original shape. The ridges and fossae of the occlusal surface have been designed by nature to form a mating surface for the opposing tooth. If the occlusion is correct, the wear rate of a restoration is limited. In a restoration which does not have the proper shape, the resulting abnormal stresses can lead to wear facets and pathological changes. Equally important is shaping the proximal surface of a restoration in order to achieve proper contact with adjacent tooth. Thus, the dentist, when placing an amalgam filling, will spend a considerable time carving and fitting the restoration. Since amalgam is easily workable for about six minutes after being packed into the tooth cavity, there is adequate time for the dentist to complete his work. On the other hand, prior art composite restorative materials have exhibited such a short time between the soft set and the hard set stage, i.e., five to thirty seconds, that the necessary hand carving and fitting is practically impossible. This disadvantage cannot be overcome by shaping of the composition after it has reached the hard set stage with the use of a drill because of difficulties in operation with extremely hard material in interproximal areas, and lack of precision.

SUMMARY OF THE INVENTION

The present invention overcomes the disadvantages of prior art composite compositions by providing composite restorative material which reaches a hard set stage a sufficient period of time after reaching the soft set stage to afford the dentist adequate time for carving and fitting of the restoration, without sacrificing the advantages of existing composite restorative materials, i.e., good marginal adaptation, high mechanical strength, aesthetics, good wear resistance, and low thermal conductivity. Furthermore, the present objectives are obtained without a concomitant lengthening of the gel period of the composition, thus avoiding inconvenience to the patient and time loss to the dentist.

More specifically, the present invention is directed to providing dental restorative compositions comprised of a conventional filler in combination with a polymerizable material consisting of at least two polymerizable groups of different reactivity. The polymerizable substance may be comprised of a bi- or poly-functional monomer having the two or more polymerizable groups within its structure, or may be comprised of a mixture of at least two monomers each containing a polymerizable group having a reactivity different from the polymerizable group on the other monomer.

DESCRIPTION OF THE PREFERRED EMBODIMENT

Dental restorative compositions of the type described in detail hereinafter are normally supplied to the dentist in two separate portions, one of these portions containing a catalyst and the other portion containing an activator for the catalyst. In using the material, the dentist mixes the two portions to form the active composition. The dentist places the freshly prepared mix into the prepared tooth cavity. Continuing polymerization of the composition causes the composition to cure to a hardness sufficient to permit carving by the dentist shortly after placing of the composition into the tooth cavity. At this stage, the composition will have a Shore D hardness of about 45 and is sufficiently hard for the dentist to carve. The mixture will continue to further polymerize, gradually becoming harder over a period of time, e.g., about six minutes, at the end of which it will reach a Shore D hardness of 85 after which it cannot be carved easily. At this stage, the composition is sufficiently hard to permit release of the patient.

The polymerizable substances of the above composition, in order to obtain the desired results of the present invention, include at least two polymerizable groups having different reactivity rates under the conditions of polymerization employed. It is not essential, however, that the two groups be of different chemical structure, since, as is well known by the skilled artisan, the reactivity of groups of the same chemical structure may be varied by the location of the groups within the structure of the compound. While the polymerizable substance of the present invention may be comprised of a single monomer or prepolymer having within its structure at least two groups having different reactivity, polymeric substances comprised of at least two monomers each of which has a group exhibiting a reactive rate different from the group of the other monomer, may also be employed.

Exemplary of monomers containing at least two groups of different reactivity are: allyl methacrylate, allyl acrylate, allyl glycidyl ether, diallyl fumarate, diallyl maleate, glycidyl methacrylate, butene-1, 4-dimethacrylate, butene-1,4-diacrylate, 4-hydroxy butene methacrylate, 4-hydroxy butene acrylate, and 1-methacryloyl-2-acryloyl-propane. Other suitable compounds will be readily apparent to the skilled artisan. With these monomers, it is possible to form compositions using only the single monomer or to use the monomer in admixture with other monomers such as the mono or diacrylates or methacrylates, for example, 2,2-bis[4'(-3"-methacryloyl-2"-hydroxy propoxy)-phenyl]propane (known as Bis/GMA), polyethylene glycol dimethacrylate, cyclohexyl methacrylate, and mixture thereof.

Instead of employing a bifunctional monomer or prepolymer, it is, as aforementioned, possible to employ two monomers containing functional groups of different reactivity. These monomers may, for example be selected from the following compounds: diglycidyl ether of bisphenol A, diallyl phthalate, mono-, di- or polyethylene or polypropylene glycol dimethacrylate, methyl methacrylate, Bis/GMA, 2-hydroxyethyl methacrylate, 2-hydroxypropyl methacrylate, glycidyl methacrylate, 2-hydroxyethyl acrylate, ethyl methacrylate, ethyl acrylate, cyclohexyl methacrylate, cyclohexyl acrylate, diallyl methacrylate, diallyl acrylate, 2-aminoethyl methacrylate, 2-aminoethyl acrylate, ethylene glycol diacrylate, diethylene glycol diacrylate, triethylene glycol diacrylate, tetra-ethylene glycol diacrylate, styrene, and triallyl cyanurate.

Suitable polymerizable substance may contain at least two polymerizable groups selected from vinyl, allyl, acryl, methacryl and styryl groups such that the composition upon polymerization would reach a Shore D hardness of about 85 at least about two minutes, and preferably about four minutes, after the composition reaches a Shore D hardness of 45 in order to afford the dentist adequate time for hand carving of the composition. Desirably, reactive groups and conditions will be selected so that the composition will reach the gel state within about two minutes after initiation of the polymerization, and a Shore D hardness of about 45 within about four minutes after initiation of the polymerization.

The fillers forming a part of the present composition are of a conventional nature and are well known within the prior art as exemplified by U.S. Pat. Nos. 3,539,533 and 3,751,399 to Lee et al. These fillers include quartz, glass, silica and various silicates which generally have a particle size from about 0.5 to about 85 microns and preferably from about 1 to about 75 microns. The compositions described herein will normally be comprised of from about 50 to about 80 percent by weight of said filler.

The compositions of the present invention may also contain other conventional additives such as curing agents, polymerization catalysts, inhibitors, antioxidants, dyes, ultraviolet absorbers, preservatives, and the like. The particular catalyst employed will depend upon the types of monomers or prepolymers comprising the composition and will be apparent to the skilled artisan.

The following examples are illustrative of the present invention and are not to be taken in limitations thereof. In each of the examples, Part A was admixed with Part B to initiate the polymerization reaction. The times necessary to reach a Shore D hardness of 45, permitting hand carving, as well as the time over which hand carving was possible, i.e., the time until the composition reached a Shore D hardness of about 85, were determined.

EXAMPLE 1

| | | |
|---|---|---|
| Allyl methacrylate | 4.0 (g) | |
| Bis-GMA | 16.0 (g) | |
| N,N-bis(2-hydroxyethyl)-p-toluidine | 0.026 (g) | Part A |
| 2-Hydroxy-4-methoxy benzophenone | 0.112 (g) | |
| 2-Isobutyl-4-hydroxytoluene | 0.012 (g) | |
| Silica | 76.7 (g) | |
| Benzoyl peroxide | 0.3 (g) | Part B |
| α-Methacrylpropyl trihydroxysilane | 2.7 (g) | |

The mix reached a Shore D hardness of 45 in three minutes at temperature of human body of 37° C., and remained easily carvable for about four minutes more. After 24 hours cure at 37° C., the compressive strength was 41,700 psi and hardness (Rockwell H) 114.

EXAMPLE 2

| | | |
|---|---|---|
| Allyl methacrylate | 8.0 (g) | |
| Bis/GMA | 12.0 (g) | |
| N,N-bis(2-hydroxyethyl)-p-toluidine | 0.026 (g) | Part A |
| 2-Hydroxy-4-methoxy benzophenone | 0.112 (g) | |
| 2-Isobutyl-4-hydroxy toluene | 0.012 (g) | |
| Silica | 76.7 (g) | |
| α-Methacrylpropyl trihydroxysilane | 2.7 (g) | Part B |
| Benzoyl peroxide | 0.3 (g) | |

The mixture, at the temperature of the human body of 37° C., reached a Shore D hardness of 45 in approximately two minutes; hand carving time was about three minutes. After 24 hours cure at 37° C., the compressive strength was 45,733 psi and hardness (Rockwell H) 114.

EXAMPLE 3

| | | |
|---|---|---|
| Allyl glycidyl ether | 8.0 (g) | |
| Bis/GMA | 12.3 (g) | |
| Diethylenetriamine ethylene oxide adduct | 0.65 (g) | Part |
| N,N-bis(2-hydroxyethyl)-p-toluidine | 0.026 (g) | A |
| 2-Isobutyl-4-hydroxy toluene | 0.0152 (g) | |
| Silica | 78.0 (g) | |
| α-Glycidoxypropyl trihydroxysilane | 3.0 (g) | Part |
| Benzoyl peroxide | 0.3 (g) | B |

The A and B components were mixed in a 1:3.5 ratio. The mix reached a Shore D hardness of 45 in three minutes at room temperature and was, thereafter, hand carvable at temperature of human body of 37° C. for four minutes. After 24 hours cure at 37° C., the compressive strength was 27,600 psi and hardness (Rockwell H) 113.

EXAMPLE 4

| | | |
|---|---|---|
| Glycidyl methacrylate | 10.0 g) | |
| Allyl methacrylate | 10.0 g) | |
| N,N-bis(2-hydroxyethyl)-p-toluidine | 0.12 g) | Part A |
| 2-Isobutyl-4-hydroxytoluene | 0.012 g) | |
| Silica | 78.0 g) | |
| α-Glycidoxypropyl trihydroxysilane | 2.56 g) | Part B |
| Benzoyl peroxide | .19 g) | |

The mixture of Parts A and B reached a Shore D hardness of 45 in about seven minutes at room temperature. Transferred to 37° C., it reached a Shore D hardness of 85 after five minutes. After a two-hour cure at 37° C., its compressive strength was 37,400 psi.

EXAMPLE 5

| | | |
|---|---|---|
| Bis/GMA | 10.6 g) | |
| Cyclohexyl methacrylate | 10.6 g) | Part A |
| N,N-bis(2-hydroxyethyl)-p-toluidine | .065 g) | |
| 2-t-butyl-5-hydroxy toluene | 0.012 g) | |
| Silica | 76.0 g) | |
| α-Glycidoxypropyl trihydroxysilane | 2.5 g) | Part B |
| Benzoyl peroxide | .19 g) | |

The mix of Parts A and B reached a Shore D hardness of 45 in 7.5 minutes at room temperature. Transferred to 37° C., it reached a Shore D hardness of 85 in 10 minutes. After a two-hour cure at 37° C., its compressive strength was 29,000 psi.

EXAMPLE 6

| | | |
|---|---|---|
| Bis/GMA | 11.4 g) | |
| Diallyl phthalate | 11.4 g) | Part A |
| N,N-bis(2-hydroxyethyl)p-toluidine | 0.07 g) | |
| 2-Isobutyl-4-hydroxy toluene | 0.012 g) | |
| Silica | 75.0 g) | |
| α-Glycidoxypropyl trihydroxysilane | 2.5 g) | Part B |
| Benzoyl peroxide | .19 g) | |

The mix of parts A and B reached a Shore D hardness of 45 in about two minutes at room temperature and a Shore D hardness of 85 in seven minutes, after transferring to temperature of 37° C. After a two-hour cure at 37° C., its compressive strength was 27,000 psi.

It will be understood that many modifications and variations of the present invention may be made without departing from the spirit and scope thereof.

What is claimed is:

1. A composition of matter useful in forming dental restoratives consisting essentially of:
   (a) from about 50% to about 80% by weight of the composition of finely divided inorganic filler particles selected from the group consisting of quartz, glass, silica, silicates, and mixtures thereof;
   (b) minor amounts of conventional additives selected from the group consisting of curing agents, inhibitors, antioxidants, dyes, ultraviolet light absorbers, preservatives, and mixtures thereof, and
   (c) as the balance of said composition, a liquid resin binder formed from a mixture of about 20% to about 40% by weight of said binder of allyl methacrylate, and the balance of said binder being 2,2-bis[4'-(3"-methacryloyl-2"-hydroxypropoxy)-phenyl]propane;

said liquid resin being polymerizable by curing agents incorporated in the composition, so that upon admixture and placement in a tooth cavity, the composition hardens in situ, polymerizing in two stages, first to a soft set condition with a Shore D hardness of 45 within about three minutes or less at human body temperature of 37° C., in which soft set condition it is carvable, then after an interval adequate to permit carving, to a hard set condition, said interval being about three to four minutes from the time the composite attains a Shore D hardness of 45 at 37° C., to the time the composite attains a Shore D hardness of 85.

2. A dental restorative composite comprising a mixture of:
   (a) from about 50% to about 80% by weight of the composite mixture of finely divided inorganic filler particles selected from the group consisting of quartz, glass, silica, silicates, and mixtures thereof,
   (b) minor amounts of conventional additives selected from the group consisting of inhibitors, antioxidants, dyes, ultraviolet light absorbers, preservatives, and mixtures thereof;
   (c) as the balance of said composite mixture, a liquid resin binder formed from a mixture of at least two monomers, one of said monomers forming 20% to 50% by weight of said binder and being selected from the group consisting of allyl methacrylate, allyl acrylate, allyl glycidyl ether, diallyl fumarate, diallyl maleate, diallyl phthalate, butene-1,4-dimethacrylate, butene-1,4-diacrylate, 4-hydroxy butene methacrylate, 4-hydroxy butene acrylate, and 1-methacryloyl-2-acryloyl-propane; and the other of said monomers forming 50% to 80% by weight of said binder and being selected from the group consisting of: 2,2-bis[4'-(3"-methacryloyl-2"-hydroxypropoxy)phenyl]propane, polyethylene glycol dimethacrylates, cyclohexyl methacrylate, and mixtures thereof; and
   (d) a free radical initiator and an activator for the initiator, these being effective to initiate polymerization of the binder;

said liquid resin binder being addition polymerizable by said free radical initiating means so that upon admixture, and placement in a tooth cavity, the composite hardens in situ, to polymerize in two stages, first to a first stage soft set condition in which it is carvable, then after an interval adequate to permit carving, to a second stage hard set condition, said interval being at least two minutes from the time the composite attains a first stage soft set Shore D hardness of 45 at 37° C., to the time the composite attains a second stage hard set Shore D hardness of 85.

3. The composite of claim 2 wherein said liquid resin binder comprises a mixture of allyl methacrylate and 2,2-bis[4'-(3"-methacryloyl-2"-hydroxypropoxy)-phenyl]propane.

4. The composite of claim 2 wherein said liquid resin binder comprises a mixture of allyl glycidyl ether and 2,2-bis[4'-(3"-methacryloyl-2"-hydroxypropoxy)-phenyl]propane.

5. The composite of claim 2 wherein said liquid resin binder comprises a mixture of cyclohexyl methacrylate and 2,2-bis[4'-(3"-methacryloyl-2"-hydroxypropoxy)-phenyl]propane.

6. The composite of claim 2 wherein the liquid resin binder comprises a mixture of diallyl phthalate and 2,2-bis [4'-(3"-methacryloyl-2"-hydroxypropoxy)-phenyl]propane.

* * * * *